United States Patent [19]

Nelson et al.

[11] Patent Number: 5,218,309
[45] Date of Patent: Jun. 8, 1993

[54] SINGLE KERNEL, SEED, NUT, OR FRUIT DIELECTRIC MOISTURE CONTENT MEASUREMENT

[75] Inventors: Stuart O. Nelson; Venkatrkrishna S. Kandala; Richard G. Leffler, all of Athens; Kurt C. Lawrence, Snellville, all of Ga.

[73] Assignee: The United States of America as represented by the Secretary of Agriculture, Washington, D.C.

[21] Appl. No.: 542,548

[22] Filed: Jun. 25, 1990

[51] Int. Cl.$^5$ ............................................ G01R 27/26
[52] U.S. Cl. .................................. 324/664; 324/667; 324/649
[58] Field of Search ............... 324/664, 667, 663, 674, 324/689, 636, 634, 630, 633, 658, 649

[56] References Cited

U.S. PATENT DOCUMENTS

| | | | |
|---|---|---|---|
| 3,155,899 | 11/1964 | Davidson | 324/667 X |
| 3,323,049 | 5/1967 | Hanken | 324/667 X |
| 3,348,140 | 10/1967 | Godding | 324/689 X |
| 4,584,522 | 4/1986 | Varela | 324/667 |
| 4,922,181 | 5/1990 | Pullan | 324/664 |
| 5,039,947 | 8/1991 | Kraszewski | 324/636 X |

OTHER PUBLICATIONS

C. V. K. Kandala et al., "Measurement of Moisture Content in Single Kernels of Peanuts: A Nondestructive Electrical Method," Paper No. 89-6103 presented at ASAE/CSAE Meeting, Quebec, PQ, Canada, Jun. 25-28, 1989, 11 pp.
C. V. K. Kandala et al., "Moisture Determination in Single Kernels of Corn—A Nondestructive Method," Trans. ASAE 31(6): 1890-1895 (Nov.-Dec. 1988).
S. O. Nelson, "Dielectric Properties of Grain and Seed in the 1 to 50-MC Range," Trans. ASAE 8(1): 38-48 (1965), Dec.

*Primary Examiner*—Jack B. Harvey
*Attorney, Agent, or Firm*—M. Howard Silverstein; Randall E. Deck; John D. Fado

[57] ABSTRACT

A method for the nondestructive measurement of the moisture content of single grain kernels, seeds, nuts, or fruits which is independent of their weight, thickness, and projected area. At least two independent parameters of complex electrical impedance or admittance of a single grain kernel, seed, nut, or fruit are measured at two different frequencies and the moisture content is calculated therefrom.

10 Claims, 1 Drawing Sheet

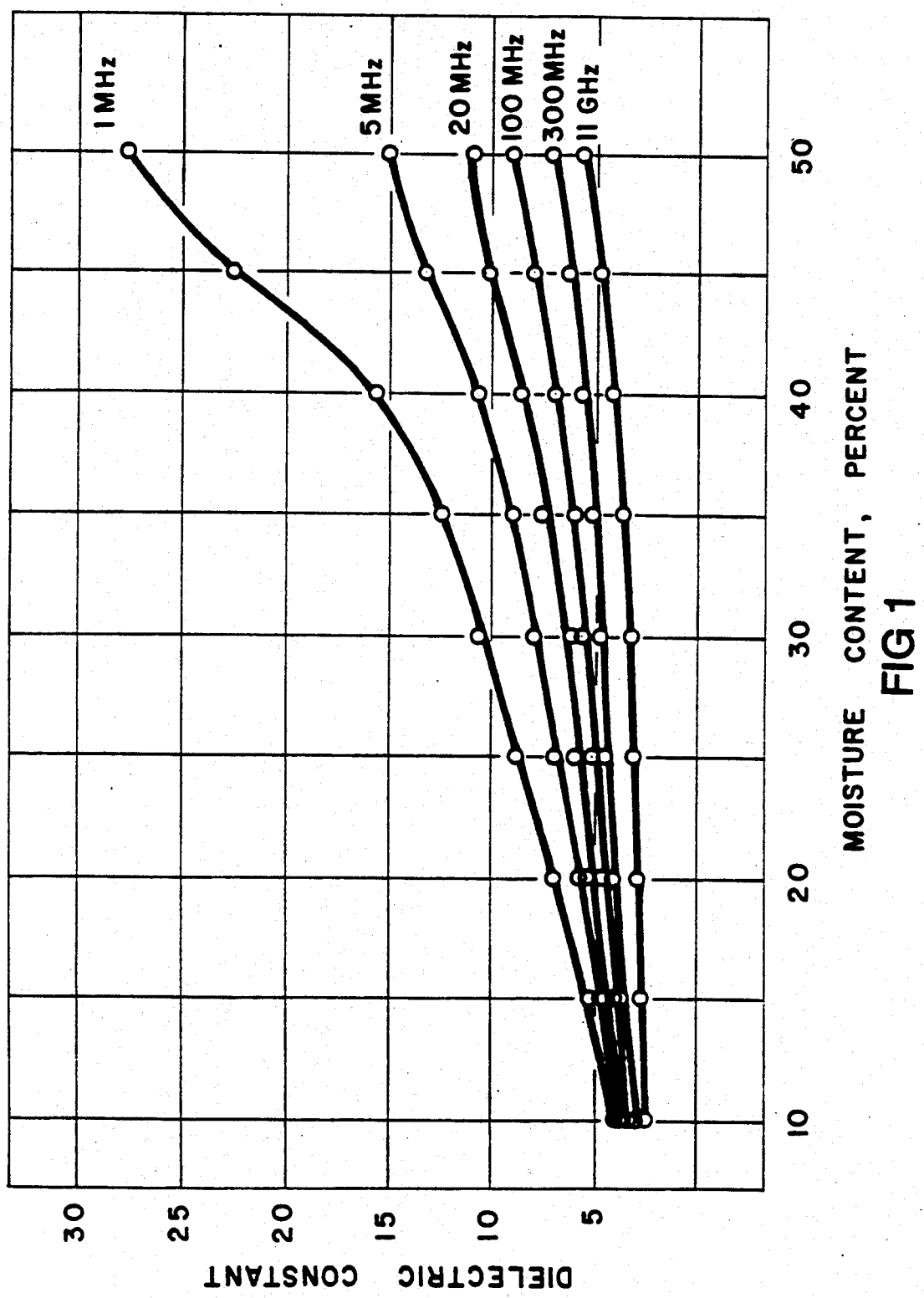

SINGLE KERNEL, SEED, NUT, OR FRUIT DIELECTRIC MOISTURE CONTENT MEASUREMENT

BACKGROUND OF THE INVENTION

1. Field of Invention

This invention relates to the nondestructive measurement of the moisture content of individual single grain kernels, seeds, nuts, or fruits.

2. Description of the Prior Art

The moisture in cereal grains, seeds, nuts, and fruits is presently measured in bulk samples, and most of the available grain moisture meters are suitable for bulk samples only. The bulk values thus measured do not always represent the moisture content of every kernel in the bulk sample and do not provide any information on the range of moisture contents of the individual kernels within the sample. Kandala [M. S. Thesis, The University of Georgia, Athens, Ga. (1987)] reported earlier that single kernel moisture content in corn (maize), Zea mays L., can vary as much as ±0.8% on a wet basis (w.b.) from the bulk value as obtained by air-oven drying tests on single kernels and bulk samples from well-conditioned corn samples. Larger variations are expected in unconditioned samples. Grain with high levels of moisture, when blended with grain of permissible levels for safe storage, can be conducive to the growth of microorganisms and may lead to spoilage. Concern has developed that spoilage of grain in transit or storage may be related to the practice of blending (mixing) of grain lots of different moisture levels.

Nelson [J. Microwave Power 13 (2): 213-218 (1978)] investigated the moisture dependence of the dielectric constant of shelled, yellow-dent field corn (maize) at different frequencies from 1 MHz to 11 GHz. Relationships established between the dielectric constant and moisture content of corn from the experimental data are shown in FIG. 1.

Measurements of capacitance and dissipation factor of a small parallel plate capacitor with single kernels of corn between and in contact with the plates have shown promise for rapidly and nondestructively measuring the moisture content of single kernels. Kandala et al. [International Agrophysics 4 (1-2): 3-12 (1988)] measured the capacitance of a parallel plate capacitor, with and without a kernel of corn between the plates, at 1.0 and 4.5 MHz. These values were used along with the kernel weight, thickness, and projected area in an equation to predict kernel moisture content within ±1% moisture on 78 to 90% of the kernels measured from different lots in the moisture range from 11 to 24%. Later, another equation was developed [Kandala et al., Trans. ASAE 31 (6): 1890-1895 (1988)] which used the dissipation factor as well as capacitance values at the same two frequencies and eliminated the need for kernel thickness and capacitance of the parallel plates without the kernel. However, measurements of the weight and projected area of the kernel were still required. This equation enabled the prediction of moisture contents over a wider range (9.5 to 26%), and predicted the moisture contents for 89% of the kernels within ±1% of the air-oven values.

Electrical resistance of single kernels between crushing roller electrodes is also used for single kernel moisture measurement, but this is a destructive process.

SUMMARY OF THE INVENTION

We have now invented a method for nondestructively determining the moisture content of single grain kernels, seeds, nuts, or fruits. According to the process, at least two independent parameters of complex electrical impedance or admittance for a single article such as a single grain kernel, seed, nut, or fruit are measured at a first frequency and a second, different frequency. The parameters measured may be independent parameters selected from the group of capacitance (C), dissipation factor (D), phase angle ($\theta$), impedance magnitude ($|Z|$), resistance (R), reactance (X), admittance magnitude ($|Y|$), conductance (G), susceptance (B), or loss angle ($\delta$). If the capacitance, dissipation factor, and phase angle were not the parameters measured, then these values are calculated algebraically at each of the frequencies. Subsequently, the moisture (M) is calculated according to the equation:

$$M = A_0 + A_1(C_1 - C_2) + A_2(C_1 - C_2)^2 + \qquad (1)$$
$$A_3 \left[ \frac{(\theta_1 - \theta_2)}{(C_1 - C_2) + k(D_1 - D_2)} - (\theta_1 - \theta_2)(C_1 - C_2) \right]$$

wherein $A_0$, $A_1$, $A_2$, and $A_3$ are constants determined by least squares computation from measurements of the electrical parameters of articles of the same kind and known moisture content.

In accordance with this discovery, it is the primary objective of this invention to provide a method and apparatus for nondestructively measuring the moisture content of single grain kernels, seeds, nuts, fruits, or other biological or agricultural products with increased accuracy. The process is particularly useful in the determination of harvesting, processing, storage, and marketing operations for agricultural products or foods as well as in research.

Another objective of the invention is to provide a method using the measurement of at least two independent parameters of complex electrical impedance or admittance at two different frequencies.

A further objective of the invention is to provide a method which is relatively independent of the mass or shape of the object or kernel measured. The determination of the moisture content is achieved without the need for measurement of the weight, thickness, or projected area of the object or kernel. In addition, the method provides good predictability over a wide range of moisture contents for articles of variable or irregular shape.

BRIEF DESCRIPTION OF THE DRAWING

FIG. 1 shows the relationship between the dielectric constant and moisture content of corn at different frequencies.

DETAILED DESCRIPTION OF THE INVENTION

The process according to the invention employs a parallel-plate electrode assembly including two electrically conducting parallel-plate electrodes, a suitable electronic circuit for measuring the high-frequency complex electrical impedance or admittance of the assembly at two different frequencies, and electronic computing equipment for calculating the moisture content from the measured complex impedance or admittance at the two frequencies.

In practice, the single article to be measured such as a single grain kernel, seed, nut, fruit, or other agricultural or botanical product is placed between the electrodes of the assembly. At least two independent electrical parameters of complex impedance or admittance are measured at each of two different frequencies, and the moisture content of the article is calculated.

Any two electrical parameters of complex impedance or admittance which are independent may be employed. These parameters are selected from the group of: capacitance (C), dissipation factor (D), phase angle ($\theta$), impedance magnitude ($|Z|$), resistance (R), reactance (X), admittance magnitude ($|Y|$), conductance (G), susceptance (B), or loss angle ($\delta$). The parameters measured at the different frequencies may be the same or different. Table I below is provided to show which of the parameters are independent and which pairs of parameters may be used. Further, other parameters, which may or may not be independent, may be measured.

TABLE I

| | \multicolumn{9}{c|}{Pairs of Independent Parameters of Complex Impedance or Magnitude} |
| | C | D | $\phi$ | $|Z|$ | R | X | $\delta$ | $|Y|$ | G | B |
|---|---|---|---|---|---|---|---|---|---|---|
| C | | Yes | Yes | Yes | Yes | No | Yes | Yes | Yes | No |
| D | | | No | Yes | Yes | Yes | No | Yes | Yes | Yes |
| $\phi$ | | | | Yes | Yes | Yes | No | Yes | Yes | Yes |
| $|Z|$ | | | | | Yes | Yes | Yes | No | Yes | Yes |
| R | | | | | | Yes | Yes | Yes | No | Yes |
| X | | | | | | | Yes | Yes | Yes | No |
| $\delta$ | | | | | | | | Yes | Yes | Yes |
| $|Y|$ | | | | | | | | | Yes | Yes |
| G | | | | | | | | | | Yes |
| B | | | | | | | | | | |

Calculation of the moisture content (M) is achieved using the equation:

$$M = A_0 + A_1(C_1 - C_2) + A_2(C_1 - C_2)^2 + \quad (1)$$
$$A_3 \left[ \frac{(\theta_1 - \theta_2)}{(C_1 - C_2) + k(D_1 - D_2)} - (\theta_1 - \theta_2)(C_1 - C_2) \right]$$

$C_n$, $\theta_n$, and $D_n$ denote the capacitance, phase angle, and dissipation factor measured at the respective frequency. The four constants $A_0$, $A_1$, $A_2$, and $A_3$ are determined by least squares computation from measurements of electrical parameters of articles of the same type and known moisture content. The constant k is equal to 1.

As indicated above, any two or more independent parameters of complex electrical impedance or admittance may be used. While measurement of C and either or both of $\theta$ or D is preferred, other parameters may be employed and then the values of C, D, and $\theta$ calculated algebraically for use in equation (1), using well known principles and identities. In this regard, it is well known that for parallel-equivalent RC circuits:

the complex
impedance $= Z = iRX/(R+iX) = [R/(i\omega C)]/[R + 1/(i\omega C)]$ (2)

and thus $|Z| = R/(i\omega CR + 1)$ (3)

and the complex admittance $= Y = G + iB$ (4)

and thus $|Y| = (G^2 + B^2)^{\frac{1}{2}}$ (5)

wherein $\omega$, the angular frequency, is determined by $\omega = 2\pi f$ where f is the frequency of the alternating voltage applied across the circuit.

Further, it is known that:

$\tan \theta = 1/D$ (6)

$|Y| = 1/|Z|$ (7)

$G = 1/R$ (8)

and $D = \tan \delta = 1/\omega CR = G/\omega C.$ (9)

For example, the capacitance and either of the dissipation factor or phase angle may be measured. The phase angle or dissipation factor not measured may then be calculated from equation (6).

Alternatively, if the resistance (R) and reactance (X) were measured, the capacitance, dissipation factor, and phase angle could be determined algebraically. From equation (2) it follows that $iX = 1/i\omega C$ and thus $X = -1/\omega C$ and $C = -1/\omega X$. Also, since $D = 1/\omega CR$ then $D = -X/R$ and $\tan \theta = (-R/X)$. The moisture content is then calculated according to equation (1).

In addition, if the admittance magnitude ($|Y|$) and phase angle ($\theta$) were measured, the capacitance and dissipation factor are again determined algebraically. From equation (6), $D = 1/\tan \theta$. From equation (5), $|Y|^2 = G^2 + B^2 = 1/R^2 + \omega^2 C^2$. From equation (9), $R = 1/(\omega CD)$, and substituting $1/(\omega CD)$ for R provides $|Y|^2 = \omega^2 C^2 D^2 + \omega^2 C^2$. Solving this equation for C and utilizing equation (6) gives $C = (|Y| \tan \theta)/[\omega(1 + \tan^2\theta)^{\frac{1}{2}}]$. The moisture content is again calculated according to equation (1).

Further, if the admittance magnitude ($|Y|$) and capacitance (C) were measured, the dissipation factor and phase angle may be determined algebraically. As shown above, $|Y|^2 = \omega^2 C^2 D^2 + \omega^2 C^2$. Solving for D gives $D = (|Y|^2 - \omega^2 C^2)^{\frac{1}{2}}/\omega C$. Since $\theta = \tan^{-1}(1/D)$ from equation (6), the moisture content is then calculated according to equation (1).

The preceding examples of combinations of measured parameters are given merely by way of illustration. Any of the combinations of parameters indicated in Table I may be employed in the determination of moisture content according to the invention.

The frequencies of the alternating voltage applied across the circuit are not critical. While the first and second frequencies are preferably within the range of about 1 MHz to about 100 MHz and frequencies of about 1 MHz and 4.5 MHz are particularly preferred, other frequencies outside this range could be used.

The process of the invention can be used to measure the moisture content of any single grain kernel, seed, nut, fruit, or other biological or agricultural product. The process is particularly applicable to the measurement of moisture content of corn, rice, soybeans, wheat, and peanuts.

EXAMPLE 1

Capacitance, dissipation factor, and phase-angle measurements were made at frequencies of 1.0 MHz and 4.5 MHz with a "Hewlett Packard" 4192A LF Impedance Analyzer, equipped with a 16096A test fixture and a specially constructed electrode assembly. The parallel-plate electrode assembly consisted of a "Plexiglas" supporting frame 12.7 mm thick, which was clamped to the test fixture, and two split-ring clamp mounting brackets, machined to accommodate a 9.5 mm shaft and mounted on the frame to support the electrode holders in vertical alignment. The two brackets were aligned with a 9.5 mm drill rod before the other components were assembled. Two 20 mm diameter circular brass electrodes were machined for threaded attachment to machined 9.5 mm Delrin rods for isolation. The electrodes were held in alignment by the two brackets. The upper electrode was maintained in contact with the kernel by the spring pressure of a gauge-head LVDT used only for convenience. Flexible wire leads connected each electrode to terminals on the frame that served for electrical connection to the test fixture. An "IBM-XT" microcomputer controlled and collected data from the impedance analyzer through an IEEE-488 interface bus.

Capacitance values read from the impedance analyzer were recorded in pF to three decimal places. The values of dissipation factor were obtained to four decimal places, and the phase angle was read in degrees to two decimal places.

EXAMPLE 2

Freshly harvested hybrid yellow-dent field corn lots were obtained from Illinois, Iowa, and Nebraska for these studies. Most of the corn lots had moisture contents of about 30%, and after being shelled, sub-lots were adjusted to lower levels by allowing them to dry in open pans at 24° C. for suitable durations. These lots of corn were then sealed in quart "Mason" jars, which were held at 4° C. for at least two weeks to equilibrate; they were agitated frequently to aid uniform distribution of moisture. Additional lower-moisture corn lots of Nebraska origin from 1985 and 1986 harvests were also used for calibration purposes. Seven moisture levels were selected between 9.5% and 26%, and the bulk moisture values of these seven lots were determined by conventional air-oven drying for 72 hr at 103° C.

Twenty kernels from each of the seven moisture lots prepared earlier were randomly selected, transferred to smaller jars, and allowed to reach room temperature. Then a single kernel was selected from one of these samples, weighed on an electronic balance to ±0.2 mg accuracy under computer control, and placed between the parallel plates of the capacitor. The capacitance, dissipation factor, and the phase angle at the two frequencies were read and stored in the computer. The procedure was repeated for each of the 20 kernels from the seven moisture lots.

After measurements were completed on all 140 kernels, the moisture content of individual kernels was determined by drying the single kernels for 72 hr at 103°. After removing them from the oven, the kernels were cooled in a desiccator and then reweighed to determine their dry weights.

The measurements were repeated on another 737 kernels which were used to test the validity of equation (1).

The four constants $A_0$, $A_1$, $A_2$, and $A_3$ were obtained by least squares computation. Thus, for any kernel, if the capacitance, dissipation factor, and phase angle are measured, the moisture content can be calculated by equation (1). In fact, only the capacitance and dissipation factor need be measured, since the phase angle can be obtained from the dissipation factor with equation (6).

The values of the constants of equation (1) are given below:

$A_0 = 11.44$, $A_1 = 27.40$, $A_2 = -11.43$, $A_3 = 0.311$.

The coefficient of determination obtained for equation (1) was 0.986.

Results of oven moisture tests on bulk samples and on single kernels showed that, although the moisture contents of individual kernels in equilibrated samples may vary as much as ±0.8% w.b., the moisture content averaged over 20 kernels was very close to the bulk value as determined by the standard air-oven method (Table II).

The moisture contents of the 140 kernels of the calibration lots were predicted by equation (1) and compared with the air-oven values for each of the seven different moisture lots as shown in Table II. The sample lots used for calibration were from harvests of different years and places. Lots 1, 2, and 6 were of Nebraska origin and harvested in 1985, 1986, and 1987, respectively. Lots 3, 4, 5, and 7 were all from the harvest of 1987, but whereas the first three were obtained from Iowa, the last one originated in Illinois. The predicted moisture content compared well with the air-oven values, agreeing within ±1% w.b. for 80 to 100% of the kernels in the different moisture groups with an average of 93% over all seven groups. The standard error of calibration was found to be 0.62% moisture.

TABLE II

Comparison of Calculated and Oven Moisture Contents of 140 Kernels from the Seven Calibration Lots, 20 Kernels in Each Moisture Lot, Using Equation (1)

| Lot No. | Bulk Sample | Oven Determination Single Kernels | | | Calculated by Eqn (1) | | | Kernels Within ±1% of Oven Moisture | |
|---|---|---|---|---|---|---|---|---|---|
| | | Mean | Std. Dev. | Range | Mean | Std. Dev. | Range | Number | % |
| 1 | 9.70 | 9.80 | 0.16 | 0.60 | 9.76 | 0.24 | 0.77 | 20 | 100 |
| 2 | 12.40 | 12.49 | 0.16 | 0.72 | 12.25 | 0.32 | 0.73 | 20 | 100 |
| 3 | 15.00 | 14.83 | 0.21 | 0.81 | 15.09 | 0.48 | 1.70 | 20 | 100 |
| 4 | 18.00 | 17.93 | 0.41 | 1.36 | 18.50 | 0.71 | 2.88 | 17 | 85 |
| 5 | 20.00 | 19.63 | 0.25 | 0.99 | 19.63 | 0.70 | 2.57 | 19 | 95 |
| 6 | 22.10 | 21.95 | 0.59 | 2.63 | 21.63 | 0.86 | 2.76 | 16 | 80 |
| 7 | 25.70 | 25.65 | 0.51 | 2.19 | 25.42 | 0.69 | 2.27 | 18 | 90 |

The moisture contents of 737 single kernels from another seven lots, which were not used earlier for calibration, as determined by oven tests and as predicted by equation (1), are summarized in Table III. Also, the first six of these lots belong to moisture groups which were different from the ones used for calibration. Lots 1, 3, and 5 originated in Nebraska whereas the rest were from Illinois. The moisture contents were predicted within ±1% w.b. for 85 to 99% of the kernels tested. The average was 91% for all 737 kernels from the seven moisture groups which ranged from 9.5 and 26%. The standard error of performance was 0.71% moisture. Thus, equation (1) was found to predict moisture contents of single kernels not only from lots of different origin but also of different years within ±1% of the air-oven values on 85% or more of the kernels for each moisture group. The method is rapid, since only capacitance and dissipation factor or phase angle are required. The moisture content predictions were independent of the origin of the material and the duration for which it was stored. Also, the accuracy did not vary much with the level of moisture content in the kernels; the ±1% predictability at the low and high moisture levels was 89% and 85%, respectively.

TABLE III

Comparison of Calculated and Oven Moisture Contents of Kernels from Seven Lots of Different Moisture Content Not Used in the Determination of the Constants of Equation (1)

| Lot No. | Bulk Sample | Oven Determination Single Kernels | | | Calculated by Eqn (1) | | | Number of Kernels Checked | Kernels Within ±1% of Oven Moisture | |
|---|---|---|---|---|---|---|---|---|---|---|
| | | Mean | Std. Dev. | Range | Mean | Std. Dev. | Range | | No. | % |
| 1 | 9.50 | 9.33 | 0.18 | 0.86 | 10.03 | 0.34 | 1.59 | 103 | 92 | 89 |
| 2 | 12.50 | 12.46 | 0.22 | 1.39 | 12.58 | 0.38 | 2.38 | 105 | 105 | 99 |
| 3 | 15.90 | 15.30 | 0.45 | 1.62 | 15.36 | 0.67 | 3.59 | 105 | 101 | 96 |
| 4 | 18.90 | 18.92 | 0.29 | 1.62 | 18.66 | 0.84 | 3.67 | 106 | 91 | 86 |
| 5 | 19.40 | 19.19 | 0.24 | 1.21 | 19.42 | 0.97 | 4.17 | 105 | 89 | 85 |
| 6 | 22.00 | 22.04 | 0.25 | 1.16 | 22.04 | 0.68 | 3.30 | 105 | 98 | 93 |
| 7 | 25.70 | 25.75 | 0.62 | 3.44 | 25.49 | 0.67 | 3.16 | 108 | 92 | 85 |

Typical data are presented in Table IV for individual kernel comparisons. Moisture contents of single kernels predicted by equation (1) (electrical measurements) and single-kernel oven-moisture contents are shown along with the differences between the two for the first 20 kernels in each of three lots of different moisture contents. Standard deviations of values calculated from the electrical measurements by equation (1) were somewhat greater than those of the single-kernel oven values, but in general they agreed quite well.

TABLE IV

Comparisons of Individual Kernel Oven-Moisture Contents and Moisture Contents Predicted by Equation (1) for the First 20 Kernels* from Three of the Seven Lots Summarized in Table III, As Indicated by Their Moisture Content

| 12.46% Single-Kernel Moisture, % | | | 19.19% Single-Kernel Moisture, % | | | 22.04% Single-Kernel Moisture, % | | |
|---|---|---|---|---|---|---|---|---|
| Oven | Eqn (1) | Diff | Oven | Eqn (1) | Diff | Oven | Eqn (1) | Diff |
| 12.65 | 12.89 | 0.24 | 19.38 | 18.76 | −0.62 | 21.71 | 20.90 | −0.81 |
| 12.24 | 12.39 | 0.15 | 19.33 | 19.86 | 0.53 | 22.53 | 22.44 | −0.09 |
| 12.48 | 12.06 | −0.42 | 18.52 | 18.24 | −0.28 | 21.63 | 22.52 | 0.89 |
| 12.43 | 12.80 | 0.37 | 19.21 | 19.32 | 0.11 | 22.08 | 21.15 | −0.93 |
| 12.03 | 12.02 | −0.01 | 19.11 | 19.71 | 0.60 | 21.84 | 21.65 | −0.19 |
| 12.45 | 12.73 | 0.28 | 19.05 | 19.48 | 0.43 | 21.84 | 22.17 | 0.33 |
| 12.33 | 12.56 | 0.23 | 19.25 | 18.41 | −0.84 | 21.65 | 22.07 | 0.42 |
| 12.67 | 12.40 | −0.27 | 18.61 | 18.35 | −0.26 | 21.99 | 23.15 | 1.16 |
| 12.99 | 13.30 | 0.31 | 19.32 | 17.51 | −1.81 | 22.18 | 22.81 | 0.63 |

TABLE IV-continued

Comparisons of Individual Kernel Oven-Moisture Contents
and Moisture Contents Predicted by Equation (1) for the First
20 Kernels* from Three of the Seven Lots Summarized in Table III,
As Indicated by Their Moisture Content

| 12.46% Single-Kernel Moisture, % | | | 19.19% Single-Kernel Moisture, % | | | 22.04% Single-Kernel Moisture, % | | |
|---|---|---|---|---|---|---|---|---|
| Oven | Eqn (1) | Diff | Oven | Eqn (1) | Diff | Oven | Eqn (1) | Diff |
| 12.18 | 12.44 | 0.26 | 18.82 | 18.20 | −0.62 | 21.80 | 20.86 | −0.94 |
| 12.64 | 12.47 | −0.17 | 19.00 | 18.30 | −0.70 | 21.98 | 22.62 | 0.64 |
| 12.42 | 13.31 | 0.89 | 19.15 | 19.87 | 0.72 | 22.27 | 22.62 | 0.35 |
| 12.59 | 12.99 | 0.40 | 18.53 | 17.96 | −0.57 | 21.93 | 20.97 | −0.96 |
| 12.68 | 12.68 | 0.00 | 18.98 | 19.47 | 0.49 | 22.22 | 21.59 | −0.63 |
| 12.74 | 13.23 | 0.49 | 18.93 | 18.95 | 0.02 | 21.83 | 22.07 | 0.24 |
| 12.58 | 12.42 | −0.16 | 19.09 | 18.07 | −1.02 | 21.76 | 21.47 | −0.29 |
| 13.00 | 12.83 | −0.17 | 18.31 | 19.82 | 1.51 | 21.57 | 20.68 | −0.89 |
| 12.44 | 12.87 | 0.43 | 18.96 | 17.59 | −1.37 | 22.02 | 22.21 | 0.19 |
| 12.52 | 12.62 | 0.10 | 18.62 | 19.14 | 0.52 | 21.37 | 21.98 | 0.61 |
| 12.46 | 13.03 | 0.57 | 18.96 | 19.80 | 0.84 | 21.98 | 21.83 | −0.15 |
| 12.53 | 12.27 | | 18.96 | 18.84 | | 21.91 | 21.89 | |
| ±0.24 | ±0.37 | | ±0.30 | ±0.80 | | ±0.27 | ±0.71 | |

*Values shown for individual kernels with mean values and standard deviations for 20 kernals.

The present invention using measurements of capacitance and dissipation factor or phase angle of single corn (maize) kernels permits the determination of moisture content in the kernel within ±1% wet basis of the air-oven value. This ±1% predictability ranges from 85 to 100% of the kernels tested in the various moisture groups with an overall mean of 91% for corn lots with moistures ranging between 9.5 and 26%.

EXAMPLE 3

Freshly harvested and shelled peanuts of the Florunner cultivar, separated into two lots according to size, were obtained for these studies from the USDA, ARS, National Peanut Laboratory at Dawson, Ga. These were procured at three different times during the 1988 harvest season. Most of these lots had a moisture content of about 25% when they were received. They were dried in open pans at room temperatures and sublots were adjusted to lower moisture contents ranging from 5 to 15%. They were sealed in quart "Mason" jars and kept in a cold room at 4° C. to equilibrate. Seven moisture levels between 5 and 15% were selected from each group. Moisture contents were determined on triplicate samples by air-oven drying for 6 hr at 130° C.

Thirty peanut kernels from each of six moisture levels, conditioned earlier and ranging between 5 and 15% moisture content were randomly selected, transferred to smaller jars, and allowed to reach room temperature. A single kernel from one lot was weighed on a "Mettler AE163" electronic balance, then placed between the parallel plates of the capacitor of Example 1, and the capacitance, phase angle, and dissipation factor were read and stored in the computer. These measurements were repeated on each of the 30 kernels from the six lots. The moisture content of each of these 180 kernels was then determined by the standard oven method. Samples were removed from the oven, cooled in a desiccator, and reweighed to obtain their dry weights. These measurements were repeated on another 210 kernels from seven of the remaining moisture lots to test the validity of equation (1).

The four constants $A_0$, $A_1$, $A_2$, and $A_3$ were obtained by least squares computation. Thus, for any kernel, if the capacitance, dissipation factor, and phase angle are measured, the estimated value of the moisture content can be calculated by equation (1).

The values of the constants of equation (1) are as follows:

$A_0 = 5.262$, $A_1 = 28.484$, $A_2 = -21.104$, $A_3 = 0.088$.

The coefficient of determination obtained for equation (1) was 0.96.

Six sample lots of peanuts were used to obtain the constants of equation (1). Equation (1) was then used to calculate the moisture content of the individual peanuts. The calculated values were compared with the air-oven values and the results are shown in Table V. Sample lots 1 and 4 were obtained during December 1988 and were of large size, classified as jumbo. Lot 6 was also obtained during the same time, while lot 5 was obtained in October, and both were of smaller size, classified as medium. Lots 2 and 3 were obtained in August and were of jumbo and medium sizes, respectively. The predicted values agreed, within ±1% moisture content (mc) with the air-oven values for 90 to 100% of the kernels in the different moisture groups which ranged from 5 to 15% mc. The average ±1% mc predictability over all moisture levels was 96%, and the Standard Error of Calibration (SEC) was 0.57% mc.

TABLE V

Comparison of Calculated [Equation (1)] and Oven Moisture
Contents of 180 Peanut Kernels from Six Calibration Lots
(30 Kernels in Each Moisture Lot)

| | Kernel Moisture Content, % | | | | | | Number of Kernels Checked | Kernels Within ±1% of Oven Moisture | |
|---|---|---|---|---|---|---|---|---|---|
| | Oven Determination | | | Calculated by Eqn (1) | | | | | |
| Lot | Mean | Std. Dev. | Range | Mean | Std. Dev. | Range | | No. | % |
| 1 | 6.02 | 0.38 | 1.76 | 6.30 | 0.08 | 0.26 | 30 | 30 | 100 |
| 2 | 7.68 | 0.30 | 1.18 | 7.71 | 0.18 | 0.75 | 30 | 30 | 100 |

TABLE V-continued

Comparison of Calculated [Equation (1)] and Oven Moisture
Contents of 180 Peanut Kernels from Six Calibration Lots
(30 Kernels in Each Moisture Lot)

| | Kernel Moisture Content, % | | | | | | Number of Kernels Checked | Kernels Within ±1% of Oven Moisture | |
|---|---|---|---|---|---|---|---|---|---|
| | Oven Determination | | | Calculated by Eqn (1) | | | | | |
| Lot | Mean | Std. Dev. | Range | Mean | Std. Dev. | Range | | No. | % |
| 3 | 8.90 | 0.37 | 1.67 | 8.88 | 0.33 | 1.18 | 30 | 29 | 97 |
| 4 | 10.52 | 0.45 | 2.37 | 10.22 | 0.54 | 2.07 | 30 | 27 | 90 |
| 5 | 11.99 | 0.53 | 2.30 | 12.18 | 0.76 | 3.06 | 30 | 29 | 97 |
| 6 | 14.65 | 0.48 | 1.94 | 14.55 | 0.53 | 1.77 | 30 | 28 | 93 |

The test group shown in Table VI consisted of seven lots of 30 kernels each with moisture contents in the same range as that of the calibration lots. None of these lots was used for calibration. Lots 1 and 4 were of the jumbo size and were obtained during August 1988. Lot 6 was also of jumbo size obtained in October 1988, whereas lots 2, 3, 5, and 7 were all obtained during December 1988. The first two were of medium size and the rest were of jumbo size. The equation worked very well for these groups, with ±1% mc predictability ranging from 90 to 100%. The average was 97% over all seven moisture levels, and the Standard Error of Performance (SEP) was 0.37% mc.

TABLE VI

Comparison of Calculated [Equation (1)] and Oven Moisture
Contents of 210 Peanut Kernels from Seven Lots of Different Moisture
Content Not Used in the Determination of Calibration Constants
(30 Kernels in Each Moisture Lot)

| | Kernel Moisture Content, % | | | | | | Number of Kernels Checked | Kernels Within ±1% of Oven Moisture | |
|---|---|---|---|---|---|---|---|---|---|
| | Oven Determination | | | Calculated by Eqn (1) | | | | | |
| Lot | Mean | Std. Dev. | Range | Mean | Std. Dev. | Range | | No. | % |
| 1 | 6.12 | 0.23 | 0.90 | 6.42 | 0.17 | 0.84 | 30 | 30 | 100 |
| 2 | 7.77 | 0.37 | 1.48 | 7.50 | 0.20 | 0.83 | 30 | 29 | 97 |
| 3 | 7.91 | 0.27 | 1.03 | 7.32 | 0.25 | 0.93 | 30 | 30 | 100 |
| 4 | 8.08 | 0.20 | 0.67 | 8.37 | 0.21 | 0.88 | 30 | 30 | 100 |
| 5 | 8.09 | 0.63 | 2.55 | 8.48 | 0.14 | 0.45 | 30 | 28 | 93 |
| 6 | 12.22 | 0.43 | 1.79 | 12.24 | 0.62 | 2.64 | 30 | 29 | 97 |
| 7 | 15.18 | 0.47 | 1.74 | 14.57 | 1.00 | 4.37 | 30 | 27 | 90 |

Typical data are presented in Table VII for individual kernel comparisons. Moisture contents of single kernels predicted by equation (1) (electrical measurements) and single-kernel oven-moisture contents are shown along with the differences between the two for 30 kernels in each of three lots of different moisture contents.

TABLE VII

Comparisons of Individual Peanut Kernel Oven-Moisture
Contents and Moisture Contents Predicted by Equation (1) for
30 Kernels* from Three of the Seven Lots Summarized in Table VI

| Lot 1 Single-Kernel Moisture, % | | | Lot 3 Single-Kernel Moisture, % | | | Lot 6 Single-Kernel Moisture, % | | |
|---|---|---|---|---|---|---|---|---|
| Oven | Eqn (1) | Diff | Oven | Eqn (1) | Diff | Oven | Eqn (1) | Diff |
| 5.76 | 5.94 | −0.18 | 7.93 | 7.62 | 0.31 | 12.67 | 12.15 | 0.52 |
| 5.92 | 6.27 | −0.35 | 7.57 | 7.31 | 0.26 | 12.08 | 13.33 | −1.25 |
| 6.18 | 6.38 | −0.20 | 8.17 | 7.74 | 0.43 | 12.29 | 12.83 | −0.54 |
| 6.22 | 6.33 | −0.11 | 7.90 | 7.78 | 0.12 | 11.72 | 11.53 | 0.19 |
| 6.09 | 6.48 | −0.39 | 7.78 | 7.15 | 0.63 | 12.13 | 11.67 | 0.46 |
| 6.27 | 6.24 | 0.03 | 7.96 | 7.35 | 0.61 | 11.87 | 12.41 | −0.54 |
| 6.02 | 6.36 | −0.34 | 8.44 | 7.55 | 0.89 | 11.90 | 12.53 | −0.63 |
| 6.23 | 6.77 | −0.54 | 7.41 | 7.16 | 0.25 | 12.29 | 12.62 | −0.33 |
| 5.94 | 6.78 | −0.84 | 7.72 | 7.09 | 0.63 | 12.53 | 12.00 | 0.53 |
| 5.95 | 6.66 | −0.71 | 7.73 | 7.30 | 0.43 | 12.41 | 12.91 | −0.50 |
| 6.22 | 6.30 | −0.08 | 7.55 | 7.07 | 0.48 | 12.52 | 13.12 | −0.60 |
| 6.24 | 6.59 | −0.35 | 7.92 | 6.86 | 1.06 | 12.41 | 11.81 | 0.60 |
| 6.15 | 6.33 | −0.18 | 7.75 | 7.41 | 0.34 | 12.99 | 12.33 | 0.66 |
| 5.82 | 6.48 | −0.66 | 7.60 | 7.13 | 0.47 | 11.61 | 11.55 | 0.06 |
| 6.03 | 6.27 | −0.24 | 7.59 | 7.24 | 0.35 | 12.48 | 11.97 | 0.51 |
| 6.65 | 6.43 | 0.22 | 7.87 | 7.30 | 0.57 | 12.48 | 11.97 | 0.51 |
| 6.09 | 6.34 | −0.25 | 7.91 | 7.33 | 0.58 | 11.86 | 11.56 | 0.30 |
| 6.40 | 6.45 | −0.05 | 7.88 | 7.09 | 0.79 | 12.40 | 12.67 | −0.27 |
| 5.97 | 6.44 | −0.47 | 8.38 | 7.32 | 1.06 | 11.72 | 12.00 | −0.28 |
| 6.57 | 6.42 | 0.15 | 8.17 | 7.10 | 1.07 | 13.32 | 13.77 | −0.44 |
| 5.80 | 6.61 | −0.81 | 7.96 | 7.57 | 0.39 | 12.66 | 11.87 | 0.79 |

TABLE VII-continued

Comparisons of Individual Peanut Kernel Oven-Moisture
Contents and Moisture Contents Predicted by Equation (1) for
30 Kernels* from Three of the Seven Lots Summarized in Table VI

| Lot 1 Single-Kernel Moisture, % | | | Lot 3 Single-Kernel Moisture, % | | | Lot 6 Single-Kernel Moisture, % | | |
|---|---|---|---|---|---|---|---|---|
| Oven | Eqn (1) | Diff | Oven | Eqn (1) | Diff | Oven | Eqn (1) | Diff |
| 5.86 | 6.31 | −0.45 | 8.12 | 7.75 | 0.37 | 12.39 | 12.42 | −0.02 |
| 6.02 | 6.54 | −0.52 | 8.16 | 7.37 | 0.79 | 11.53 | 12.46 | −0.93 |
| 6.66 | 6.34 | 0.32 | 8.12 | 7.17 | 0.95 | 12.14 | 11.62 | 0.52 |
| 5.96 | 6.28 | −0.32 | 7.99 | 7.13 | 0.86 | 12.10 | 11.19 | 0.91 |
| 6.26 | 6.63 | −0.37 | 7.90 | 7.53 | 0.37 | 12.08 | 12.95 | −0.87 |
| 6.00 | 6.50 | −0.50 | 8.20 | 7.33 | 0.88 | 11.63 | 11.13 | 0.50 |
| 6.14 | 6.45 | −0.31 | 7.42 | 6.90 | 0.52 | 12.56 | 12.10 | 0.47 |
| 6.22 | 6.29 | −0.07 | 8.37 | 7.77 | 0.60 | 11.56 | 12.33 | −0.77 |
| 6.06 | 6.31 | −0.25 | 7.69 | 7.21 | 0.48 | 12.27 | 12.29 | −0.02 |
| 6.12 | 6.42 | −0.29 | 7.91 | 7.32 | 0.58 | 12.22 | 12.24 | −0.02 |
| ±0.23 | ±0.17 | ±0.29 | ±0.27 | ±0.25 | ±0.26 | ±0.43 | ±0.62 | ±0.59 |

*Values shown for individual kernels with mean values and standard deviations for 30 kernels.

The present invention using measurements of peanuts permits the determination of the moisture content in the peanut within ±1% of the air-oven value. This ±1% predictability averaged 97% of the peanuts tested in the moisture range from 5 to 15% and was 90% or better for any one lot in this range. The method worked well for different sizes and shapes of kernels and was found to be independent of the time of harvest and duration of storage in a cold room.

It is understood that the foregoing examples and detailed description are given merely by way of illustration and that variations may be made therein without departing from the spirit and scope of the invention. For example, a nonparallel electrode arrangement may be employed, as could nonplanar electrodes. Further, one skilled in the art would recognize that equations other than equation (1) could be derived and employed to determine the moisture content from the measured parameters.

I claim:

1. A nondestructive process for determining the moisture content of single grain kernels, seeds, nuts, fruits, or other botanical or agricultural products comprising:
    (a) placing a single article selected from the group consisting of grain kernels, seeds, nuts, fruits, and other botanical and agricultural products, between two electrically conducting parallel-plate electrodes, said electrodes connected in an electronic circuit for measuring parameters of electrical impedance or admittance at two different frequencies;
    (b) at a first frequency, $f_1$, measuring at least two independent electrical parameters selected from the group consisting of capacitance, C, dissipation factor, D, phase angle, $\theta$, impedance magnitude, $|Z|$, resistance, R, reactance, X, admittance magnitude, $|Y|$, conductance, G, susceptance, B, and loss angle, $\delta$, for said single article;
    (c) at a second frequency, $f_2$, different from said first frequency measuring at least two of said independent electrical parameters of said article;
    (d) if not measured in steps (b) or (c) calculating the capacitance, $C_1$ and $C_2$, dissipation factor, $D_1$ and $D_2$, and phase angle, $\theta_1$ and $\theta_2$, at each of said first and second frequencies, respectively, from said electrical parameters measured in steps (b) and (c);
    (e) determining the moisture content, M, of said article from said capacitance, $C_1$ and $C_2$, dissipation factor, $D_1$ and $D_2$, and phase angle, $\theta_1$ and $\theta_2$, and wherein the weight, thickness, and/or projected area of said article are not measured and are not employed in the determination of the moisture.

2. The process of claim 1 wherein said independent electrical parameters measured in said steps (b) and (c) are the capacitance, $C_1$ and $C_2$, dissipation factor, $D_1$ and $D_2$, and phase angle, $\theta_1$ and $\theta_2$.

3. The process of claim 1 wherein said independent electrical parameters measured in said steps (b) and (c) are the capacitance, $C_1$ and $C_2$, and one of the dissipation factor, $D_1$ and $D_2$, or phase angle, $\theta_1$ and $\theta_2$, and in said step (d) the remaining parameter of said dissipation factor, $D_1$ and $D_2$, or said phase angle, $\theta_1$ and $\theta_2$, is calculated at each of said first and second frequencies according to the relation: $\tan \theta = 1/D$.

4. The process of claim 1 wherein said first and second frequencies are within the range of about 1 MHz to 100 MHz.

5. The process of claim 4 wherein said first frequency is about 1 MHz and said second frequency is about 4.5 MHz.

6. The process of claim 1 wherein said first frequency is less than 1 MHz and said second frequency is less than 1 MHz.

7. The process of claim 1 wherein said first frequency is greater than 100 MHz and said second frequency is greater than 100 MHz.

8. The process of claim 1 wherein the moisture of said article is between about 9.5 and about 26%.

9. The process of claim 1 wherein said grain kernel is corn.

10. The process of claim 1 wherein said seed is a peanut.

* * * * *